(12) United States Patent
Dey et al.

(10) Patent No.: US 11,278,275 B2
(45) Date of Patent: Mar. 22, 2022

(54) UNIVERSAL WINDING MACHINE FOR A MULTITUDE OF TRAY DESIGNS

(71) Applicant: Harro Höfliger Verpackungsmaschinen GmbH, Allmersbach im Tal (DE)

(72) Inventors: Clifford Dey, Allmersbach im Tal (DE); Ingmar Neff, Allmersbach im Tal (DE); Sven Brecht, Allmersbach im Tal (DE); Marcel Renz, Allmersbach im Tal (DE); Jürgen Gattnar, Allmersbach im Tal (DE)

(73) Assignee: Harra Höfliger Verpackungsmaschinen GmbH, Allmorsbach im Tal (DE)

( * ) Notice: Subject to any disclaimer, the term of this patent is extended or adjusted under 35 U.S.C. 154(b) by 268 days.

(21) Appl. No.: 16/564,000

(22) Filed: Sep. 9, 2019

(65) Prior Publication Data

US 2020/0079543 A1    Mar. 12, 2020

(30) Foreign Application Priority Data

Sep. 10, 2018 (EP) .................................... 18193349

(51) Int. Cl.
*B65B 63/04* (2006.01)
*B65B 19/34* (2006.01)
(Continued)

(52) U.S. Cl.
CPC .. *A61B 17/06004* (2013.01); *A61B 17/06114* (2013.01); *B65B 19/34* (2013.01);
(Continued)

(58) Field of Classification Search
CPC ........ A61B 17/06004; A61B 17/06114; A61B 2017/00526; A61B 17/06133
See application file for complete search history.

(56) References Cited

U.S. PATENT DOCUMENTS 5,487,216 A *  1/1996  Demarest .........  A61B 17/06133
                                                              29/705
5,660,024 A     8/1997  Ivanov et al.
(Continued)

FOREIGN PATENT DOCUMENTS

| EP | 0760227 A1 | 3/1997 |
| EP | 0676172 B1 | 8/1998 |
| EP | 3153117 A1 | 4/2017 |

*Primary Examiner* — Robert F Long
*Assistant Examiner* — Xavier A Madison
(74) *Attorney, Agent, or Firm* — Smartpat PLC (57) ABSTRACT

A machine for winding sutures into a suture tray package comprises a base platform, a plurality of package nests, a first workstation for placing an empty tray onto one of the package nests, a further workstation for feeding a needle with an attached suture in the tray and parking said needle in the tray, a winding station for winding the suture into a winding channel of the tray, a lid placement station for placing a lid onto one of the package nests, a lid attachment station for attaching the lid to the tray, and an offloading station for removing said trays from the package nests. The further workstation comprises two tweezer grippers, at least one of said tweezer grippers having a V- or U-shaped notch, said V- or U-shaped notch being located at the inside of the notched tweezer gripper facing the second tweezer gripper.

11 Claims, 5 Drawing Sheets

(51) Int. Cl.
  *B65B 35/10*  (2006.01)
  *A61B 17/06*  (2006.01)
  *A61B 17/00*  (2006.01)

(52) U.S. Cl.
  CPC .............. *B65B 35/10* (2013.01); *B65B 63/04* (2013.01); *A61B 17/06133* (2013.01); *A61B 2017/00526* (2013.01); *A61B 2017/06147* (2013.01)

(56) References Cited

U.S. PATENT DOCUMENTS

| | | | |
|---|---|---|---|
| 5,661,954 A * | 9/1997 | Ivanov | B65B 35/26 53/116 |
| 5,664,404 A * | 9/1997 | Ivanov | B65B 19/34 53/430 |
| 5,788,062 A | 8/1998 | Cerwin et al. | |
| 5,920,482 A * | 7/1999 | Demarest | A61B 17/06004 700/159 |
| 5,964,075 A | 10/1999 | Daniele et al. | |
| 5,970,686 A * | 10/1999 | Demarest | B65B 63/04 53/118 |
| 6,012,216 A | 1/2000 | Esteves et al. | |
| 6,014,851 A * | 1/2000 | Daniele | B65B 5/04 53/118 |
| 6,081,981 A * | 7/2000 | Demarest | A61B 17/06004 29/407.04 |
| 6,115,650 A | 9/2000 | Demarest et al. | |
| 6,463,719 B2 * | 10/2002 | Dey | A61B 17/06133 206/63.3 |
| 6,804,937 B2 | 10/2004 | Dey et al. | |
| 6,807,796 B1 | 10/2004 | Dey et al. | |
| 2004/0177594 A1* | 9/2004 | Dey | A61B 17/06133 53/430 |
| 2010/0139351 A1 | 6/2010 | Bruhin | |
| 2014/0005676 A1 | 1/2014 | Shelton et al. | |
| 2016/0317148 A1 | 11/2016 | Martinez | |
| 2017/0174372 A1 | 6/2017 | Quinones | |
| 2019/0039769 A1* | 2/2019 | Dey | B65H 54/58 |

* cited by examiner

UNIVERSAL WINDING MACHINE FOR A MULTITUDE OF TRAY DESIGNS

TECHNICAL FIELD

This disclosure relates to packages for surgical sutures and surgical needles, more particularly to equipment for winding surgical sutures and attached surgical needles into suture packages. Conventional surgical suture and needle packages serve several useful functions, including protecting the needles and sutures during handling, shipping, and storage. In addition, the packages facilitate access and release of the needles and sutures during surgery or other medical procedures prior to application. Furthermore, this disclosure relates to equipment for attaching surgical sutures to needles and loading them into a winding machine.

BACKGROUND

Surgical needles and attached surgical sutures are well known in the art. Surgical needles and sutures are packaged in a variety of packages for delivery of the needles and sutures to the surgeon. The packages need to have a number of important characteristics, including ease of loading, ease of dispensing, and protection of the needle and the suture during handling, sterilization, shipping and storage.

Surgical sutures are packaged in tray packages by using conventional winding fixtures. The fixture typically has a rotatable base with mounting pins. A tray package is mounted on the base and the pins such that the top of the tray package is facing upwardly. Then a winding stylus mounted to a winding head directs a length of suture down into a track of the suture tray. As the tray rotates the stylus rides or touches the bottom thereby opening the upper or lid flaps so that the suture is placed in the track in a uniform manner, Examples of such winding fixtures and styluses are disclosed in U.S. Pat. Nos. 5,660,024, 5,664,404, 6,804,937, and 6,463,719. In these cases, the automated winding processes where the needle is automatically placed in the suture tray and then automatically wound are limited to single arm sutures of about 5/0 and above. The double armed sutures are typically hand placed in a plastic tray or a paper tray. The sutures in the smaller sizes are typically also hand placed in a foam retainer on a paper tray.

Therefore, there is a need in this art to automatically load and wind micro needles and micro sutures as well as double armed sutures that cannot be attached automatically.

Attaching surgical sutures to needles is also well known in the art. Surgical needles and sutures have historically been attached by hand with a setup time between 20 and 30 minutes using a simple crimping die. The manual operators are typically able to handle five to six parts per minute. This manual process has the suture and needle combination handed off to either a manual hand winding process, or the combination can be hand fed into an automatic winding machine. There are some attached swage wind combinations, but these cannot be hand fed into an automatic winding machine. These swage wind combinations typically have expensive swage tools that can require up to 120 minutes for changeover and setup.

The machines currently in use for automatically attaching needles to suture are usually quite slow. Approximately, seven to ten parts can be attached per minute and the machines require 45 to 60 minutes to be set up. Automated equipment can require up to two hours for changeover.

Winding sutures into the tray is well known in the art. But the current designs have a speed limiting factor along with premature wear as the RPM (rounds per minute) of the winding is increased.

There is a need in this art for a novel automated suture attaching and tray winding process that overcomes the deficiencies of the prior art. Furthermore, there is a need in this art to shorten the changeover time from a large needle suture combination to a small needle suture combination.

SUMMARY

Proceeding from this previously known prior art, it is an object of the present disclosure to provide a novel suture winding machine with allows for automatically loading and winding micro needles and micro sutures and which can be easily adapted from automatically loading to manual loading in order to allow for faster winding of the suture.

Accordingly, a novel adaptive suture and tray process is disclosed. This process starts with a multi station machine. It can be circular or inline and can contain as many stations as desired. The preferred embodiment is an eight station rotary type machine. The machine has a top plate with modular mounting holes for off the shelf stations as required by the intended use.

The first station would be for the infeed of the desired tray using existing methods and devices.

The second station is fundamentally open for custom modules required for packages such as pre-arming a needle retention area or adding a piece of foam for small needles. This station could also provide confirmation of tray present.

The third station is for feeding a needle in the tray and parking said needle in the tray. In order to allow for micro needles to be gripped, this station comprises two tweezer grippers. At least one of said tweezer grippers has a V- or U-shaped notch, said V- or U-shaped notch being located at the inside of the notched tweezer gripper facing the second tweezer gripper. Additionally, station 3 comprises at least two infeed lines for receiving infeed slides with needles and attached sutures. One of the infeed lines may come from an automated crimping unit where the sutures are automatically attached to the needles and the resulting combination is automatically placed on an infeed slide. The second one of the infeed lines may come from a manual loading station where the needles with attached suture are manually loaded onto the infeed slides.

The infeed lines can both end at identical positions at the third station. Preferably, the infeed lines end at different positions at the third station. In this case, the gripping position of the robot grippers has to be adjustable in order to accommodate the different ending positions of the infeed lines.

Station 4 is a suture winding assembly. The suture winding assembly has a nest member for receiving a suture tray package having a winding channel. The assembly can provide a vacuum for assisting the winding of the sutures into a one-piece bottom tray. The assembly also has a winding head for rotability and engaging the nest and tray package. Furthermore, the winding assembly has a suture control arm with a base member. The suture control arm can have a top side and a bottom side with a frontal opening mechanism fundamentally in a rounded shape. Furthermore, there can be a U-shaped member at the rear of the suture control arm that controls the entry point and the height of the suture. The rotatable winding head has an outer ring structure and an inner ring structure, said outer ring structure and said inner ring structure being spaced apart from each other at a constant distance to each other. The suture control arm has a single running guide bearing, said running guide bearing being mounted between the inner ring structure and the outer ring structure of the winding head. This allows the assembly to be run at speeds above 500 RPM without showing significant wear due to reducing torsional effects on the bearings and guiding ring.

Station 5 is for the lid placement. Either a paper lid or a plastic top can be placed by this station.

Station 6 is for the lid attachment. For example, there could be either staking or ultrasonic attachment. When the winding of the suture is performed under vacuum, station 4 is usually followed by station 5 and station 6. Nevertheless, if the winding of the suture is done without vacuum, it can be advantageous to have station 5 followed by station 6 and only then followed by station 4.

Station 7 is the offload station to an intermediate station. In this station, a camera inspection can be completed. There can be an offload to either an outfeed belt, a magazine or a rejection bin. It can be advantageous to have a demagnetisation of the needle before offloading the tray.

Station 8 will be used for the verification of a successful unloading operation.

The vacuum can be supplied in a constant manner from station 4 to station 6 as required by the package design.

Furthermore, a novel apparatus for attaching surgical sutures to needles and loading them into a winding machine is disclosed.

The needle suture attaching machine of this apparatus has a novel die setup arrangement. Most dies vary in height due to rework and it can take quite some time to offset this variance. Therefore, the present machine has a digital measuring station to measure the height of the die. The measurements can then be downloaded to the suture attaching station where it is normalized to a set zero point. Alternatively, the measurements can be manually entered at the HMI. This method reduces the setup time of the crimping die to a maximum of five minutes, keeping changeover to a minimum. This measuring station could be offline. The rest of the automatic crimping is well known in the art, but the footprint has been reduced by simplifying the suture infeed process.

The interface between the suture attaching machine and the winding machine is a hand off to one of two infeed lines. One of the infeed lines is a straight motion to the winding machine with its robot grippers for gripping the needles and placing them into a needle park or a foam park of the tray. When this infeed line is not in use, the suture attaching machine offloads to a bin where the needle and suture combinations are stacked into bundles and can be manually offloaded. The second one of the infeed lines is at a 90-degree angle to allow for hand feeding of bundles needle and suture combinations. In this case, the sutures could have been hand crimped because of the small batch size or because they are a combination smaller than USP 5/0.

The infeed slides of the infeed lines allow for the manual placing of the needle to be transported to the pickup station of the winding machine. This is designed to accommodate single and double armed sutures down to 5/0 and single arm sutures below 5/0. With a quick change of the robot grippers it could also accommodate needles down to 8 millimetres to 8/0 sutures.

These and other features and advantages of the present invention will become more apparent from the following description and accompanying drawings.

Further advantages and features of the invention can be gathered from the features which are further specified in the claims and from the following exemplary embodiments.

BRIEF DESCRIPTION OF THE DRAWINGS

In the following text, the invention will be described and explained in greater detail using the exemplary embodiments which are shown in the drawings.

DETAILED DESCRIPTION

Figure 1:
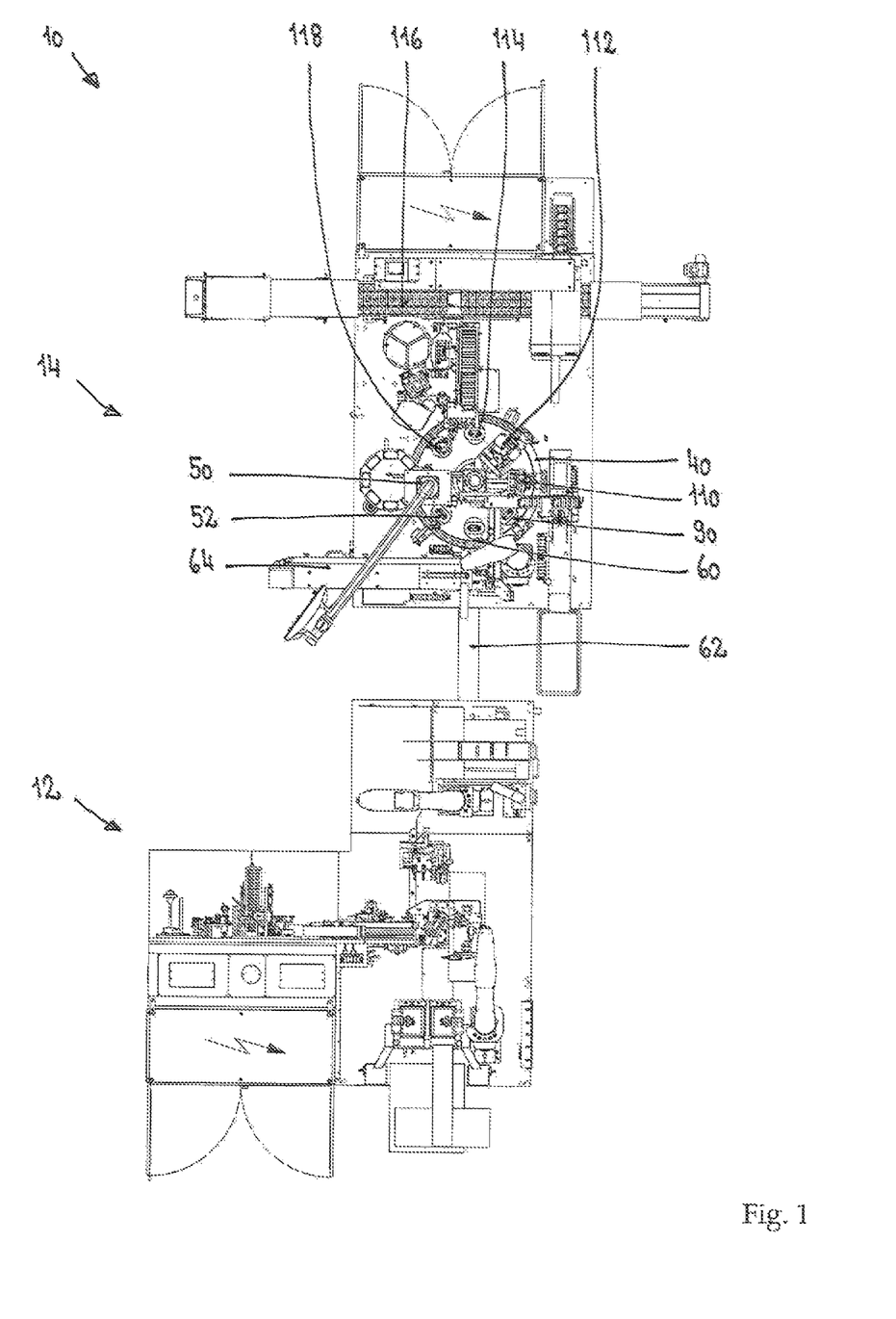
FIG. 1 is a schematic view of the winding machine with suture attaching machine.

The combined machine 10 according to FIG. 1 consists of two main units, the first unit being a suture attaching machine 12 and the second unit being a winding machine 14.

Figure 2:
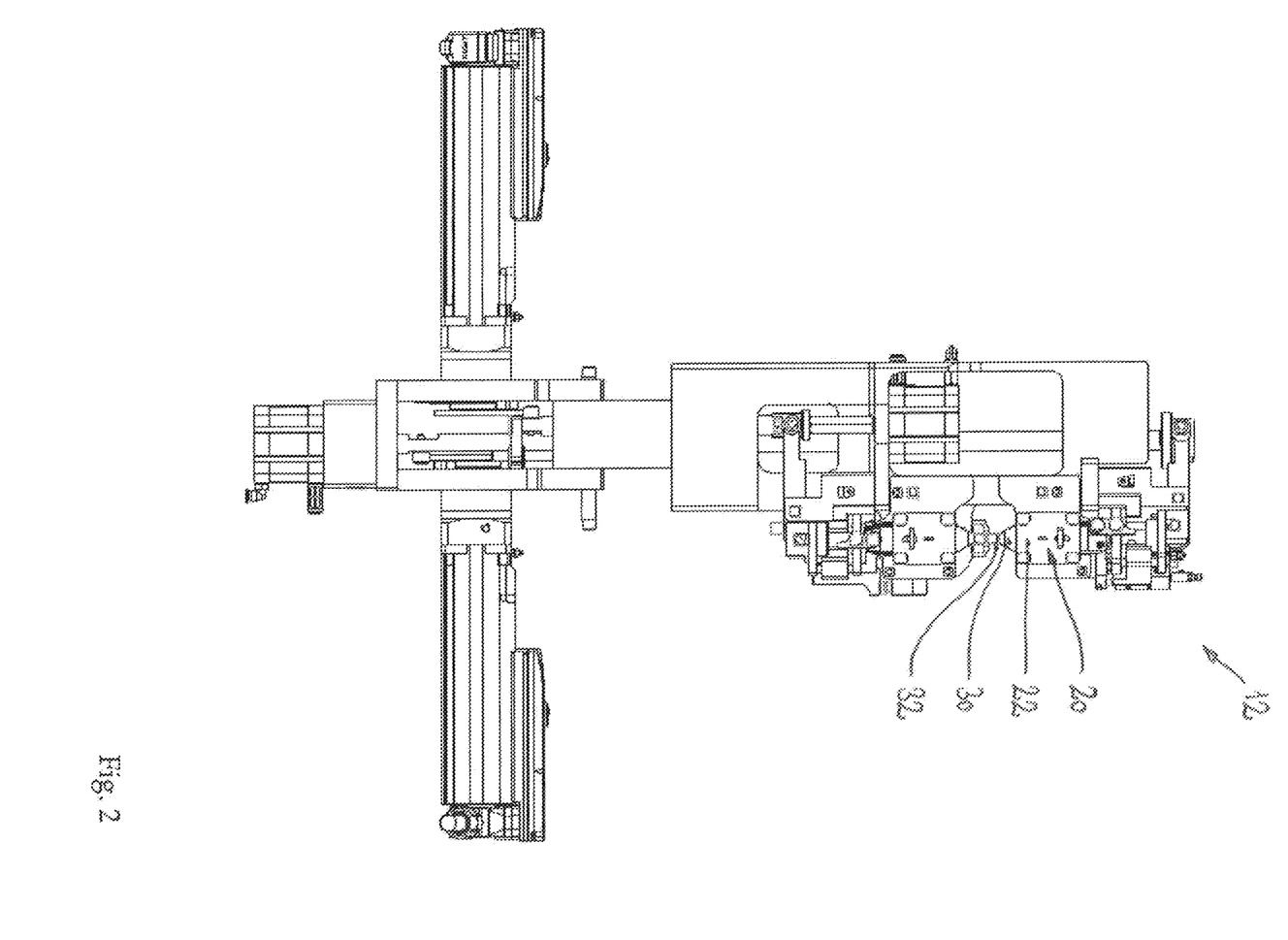
FIG. 2 is a schematic view of the suture attaching machine according to FIG. 1.
Figure 3:
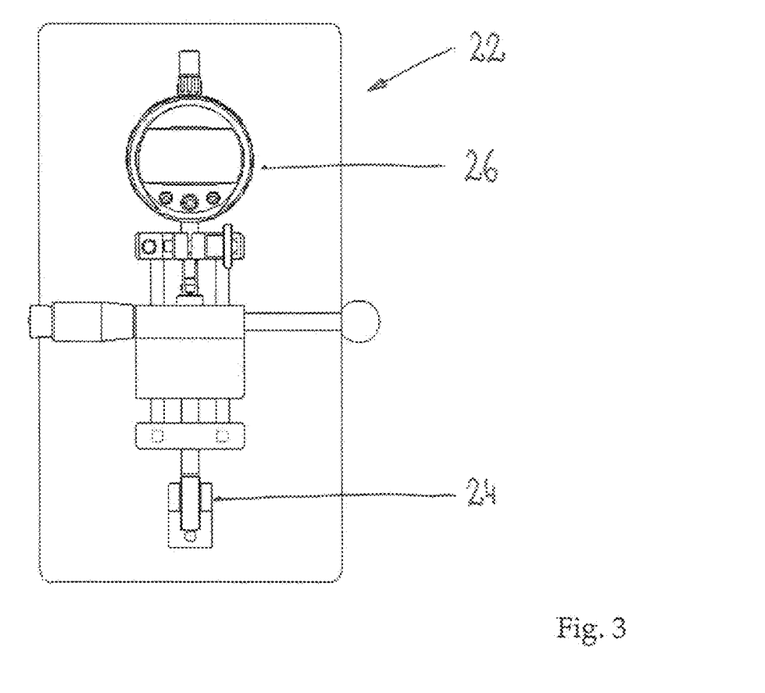
FIG. 3 is a schematic view of the offline measuring fixture of the suture attaching machine.

The suture attaching machine 12 attaches the needle and suture to form a single combination. This machine 12 is shown in greater detail in FIG. 2. The setup of the crimping unit 20 is facilitated by using an offline measuring fixture 22 which is shown in FIG. 3. The offline measuring fixture 22 is calibrated by placing a precision gage block 24 into the measuring fixture 22 and then zeroing the digital measuring unit 26. The gage block 24 is then replaced by the desired crimping die 30 and the reading is noted as an offset for the servo drive of the suture attaching machine 12. This offset is used to set the zero point of the crimping die centre 32.

The needle and suture combination is then transferred to the winding machine 14, which is preferred to be inline but can be at any angle. Referring to FIG. 1, the winding machine 14 has a base platform 40 with a rotary dial 42 mounted thereon. In this preferred embodiment there are eight package nests 44 on the rotary dial 42. Each of the package nests 44 is labelled so it will be possible to track the trays during the winding process. There could be more than eight package nests 44 or less than this, depending on the number of stations necessary for the winding process.

This type of rotary dial 42 is widely used in the art so it is not described in detail. On the outside of the rotary dial 42 is the base plate 46 for mounting each of the stations. This modular design allows for quick customization of the stations as may be required by the design of the tray or by station requirements.

The first station 50 is the tray infeed. This station 50 is shown at nine o'clock of the rotary dial 42 according to FIG. 1. This type of infeed station 50 is widely used in the art so it is not described in detail. In principal, there are two options. There could be a single stack of trays to be loaded into the package nests 44 or there could be a multi stack carrousel. In both cases the trays are singularized and placed onto the package nests 44.

In the shown embodiment, the package nests 44 are rotated in an anticlockwise direction. The second station 52 is an open station for further options. For example, this station 52 could be used to load a top of the tray. It would also be possible to cut and place a foam in this station 52. If micro-needles do not fit into the needle park of the tray, such a foam might be necessary.

Figure 4:
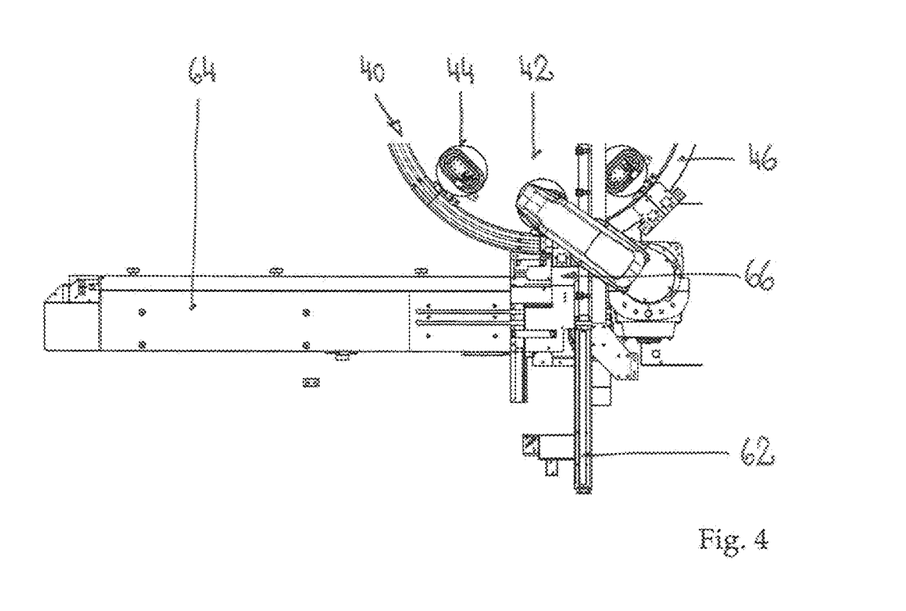
FIG. 4 is a schematic view of the two infeed lines of the winding machine according to FIG. 1.

In the third station 60 the needle with an attached suture is fed in and parked in the tray. The third station 60 comprises two infeed lines 62, 64 (see FIG. 4). The infeed lines 62, 64 are positioned at 90-degree angle to each other. The primary infeed line 62 is used for the transfer from the suture attaching machine 12 to the winding machine 14.

Figure 5:
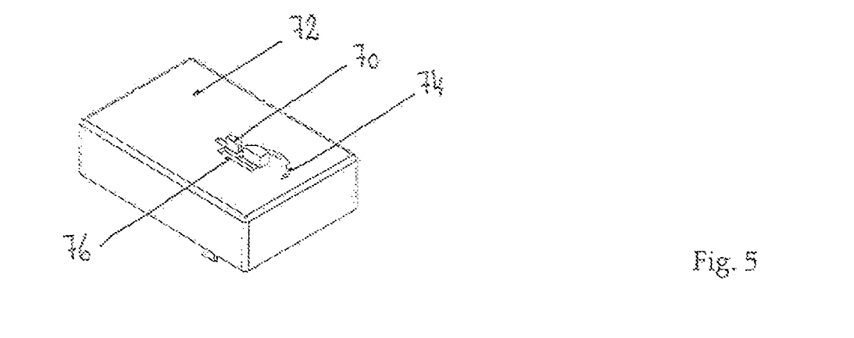
FIG. 5 is a schematic view of an infeed slide for transporting the needle to station 3 of the winding machine.

The secondary infeed line 64 is used for manual loading of a needle when switched to stand alone mode. In this case, an operator loads the needle into an infeed clamp 70 located on an infeed slide 72 of the infeed line 64 (see FIG. 5). When loading needles above 15 millimetres in length the needle is positioned with the clamp 70 preferably in the centre of the curve. When loading needles 74 smaller than 15 millimetres the needles 74 are loaded with the barrel in the clamp 70 as shown in FIG. 5.

The infeed slides 72 of infeed line 64 as well as the infeed slides of infeed line 62 then move to the pickup station 66 of station 3. Infeed slides like this are widely used in the art so they are not described in detail. At the pickup station 66 robot grippers 80 grip the needles 74 from the infeed slides 72 (see FIG. 6). The slide 72 then returns to its loading position. The robot grippers 80 now travel to the package nest 44 of the rotary dial 22 and load the needle 74 into a needle park of the tray (see FIG. 7).

Figure 6:
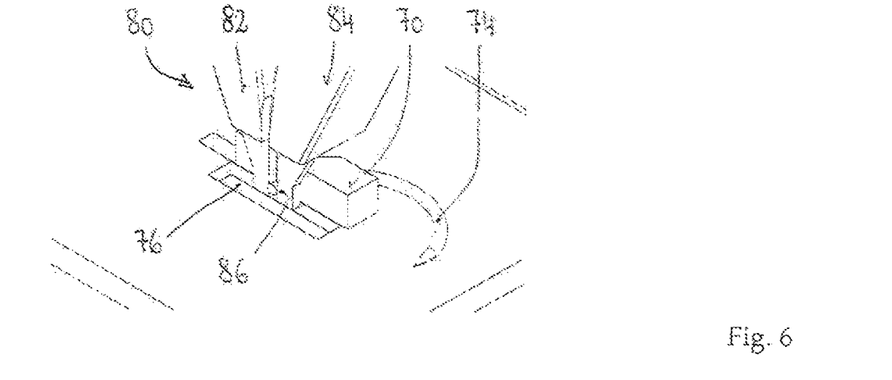
FIG. 6 is a schematic view of the tweezer grippers of station 3 of the winding machine gripping the needle from the infeed slide.

When loading small needles 74 also known as micro needles 74 a special pair of grippers 80 is used. In this case, two tweezer grippers 82, 84 are used. One of the tweezer grippers 84 has a V-shaped notch 86 to keep the needle 74 from rotating during the transfer. In order to grip the needle 74 the tweezer grippers 84 can dip into a cavity 76 in front of the infeed clamp 70.

Figure 7:
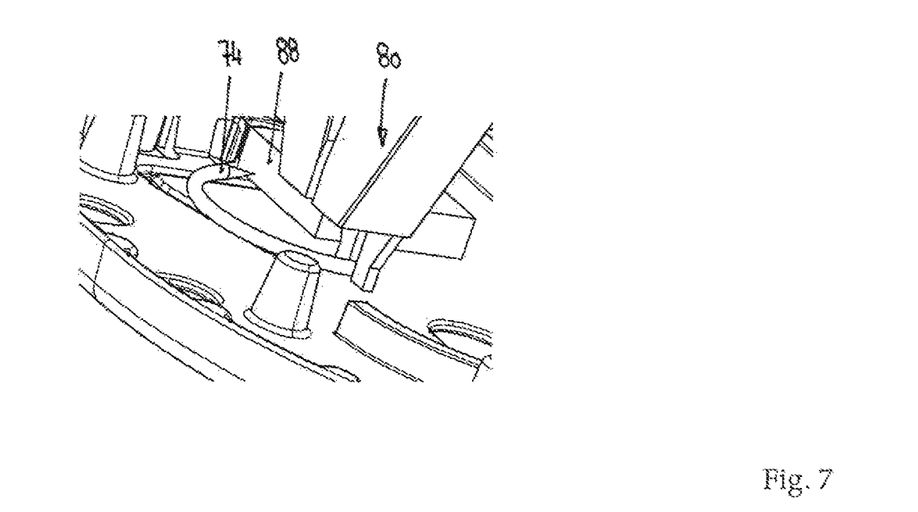
FIG. 7 is a schematic view of the tweezer grippers placing the gripped needle into a foam park.

The tweezer grippers 82, 84 then transport the needle 74 with attached suture to the third station 60 for parking the needle 74 into a foam park 88. The foam park 88 can be attached to the tray at the second station 52 and it can be of any shape. The tweezer grippers 82, 84 then insert the needle 74 along an edge of the foam park 88 to approximately the mid distance of the height of the foam park 88. The tweezer grippers 82, 84 rotate the needle 74 into the foam park to securely insert the needle 74. The tweezer grippers 82, 84 then release the needle 74. The needle 74 is left inserted into the foam park 88 leaving the point of the needle 74 protected.

The fourth station 90 is the winding station. This station 90 is shown in greater detail in FIGS. 8 and 9. The winding station 90 has a winding head 92. The winding head 92 has an outer ring structure 94 and an inner ring structure 96. At the outer ring structure 94 there is a roller bearing 98. A suture control arm 100 is mounted to a base member 102. The base member 102 is equipped with a running guide bearing 104. The outer ring structure 94 along with the roller bearing 98 maintains the relative relationship between the base member 102 of the suture control arm 100 and the inner ring structure 96. For this purpose, the running guide bearing 104 is piloted by the inner ring structure 96. During the winding process, the winding head 92 is rotated. The base member 102 of the suture control arm 100 is not rotated but it can adapt to the relative position of the winding head 92.

Figure 8:
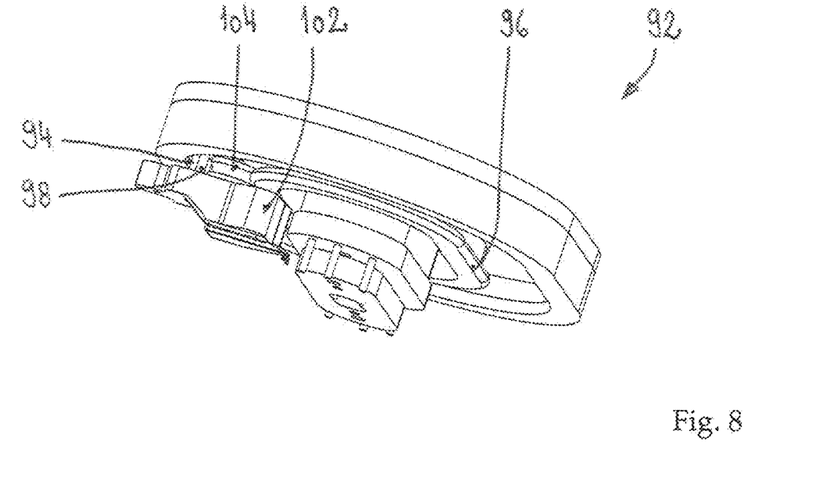
FIG. 8 is a schematic view of the novel winding head of station 4 of the winding machine.
Figure 9:
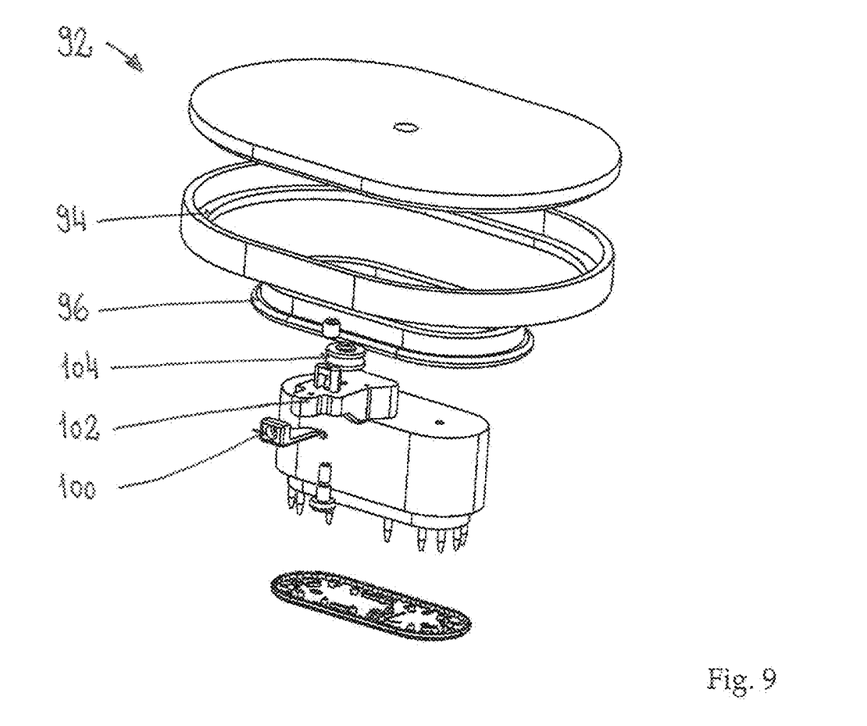
FIG. 9 is an exploded view showing the winding head according to FIG. 8.

This winding station 90 can wind trays with vacuum present or without vacuum present. If there is no vacuum present during the winding, it is usually necessary to have the lid placed directly after the needle parking and before starting the winding of the suture. Therefore, in this case the fifth station 110 together with the sixth station 112 should be placed after the third station 60 and before the winding station 90.

The fifth station 110 is a printing and lid placement station. The lids could be pre-printed paper lids of plastic lids or the like. This type of station 110 is widely used in the art so it is not described in detail.

The sixth station 112 is the lid attachment station. The lid could be attached by using ultrasonic sound or heated die, for example. By using ultrasonic sound or heated die it is possible to deform the standoff members of the trays, thereby locking the lid in place. This type of station 112 is widely used in the art so it is not described in detail.

The seventh station 114 is an offloading station. After offloading, the trays are usually transported to an intermediate inspection station (not shown). This type of station 114 is widely used in the art so it is not described in detail. The intermediate inspection station is usually the station where all camera inspections are performed. The tray is then transferred to an outfeed section 116 which can be a belt or a magazine, for example. It could also be transferred to a reject area. It can be advantageous to have a demagnetisation of the needle before offloading the tray.

This kind of intermediate inspection station is widely used in the art so it is not described in detail.

The eighth station 118 is an open station for further options. For example, this station 118 could be used for a camera check in order to confirm the offloading of the tray.

In contrast to the circular layout of the rotary dial 42, there could also be an inline form for the suture winding machine 14. It is also possible to have a combination of a rotary dial 42 and an inline form. The winding process of the present invention can be used with tray suture packages of various designs. The shape of the tray 14 can be essentially circular to oval. It can also be oval with finger indentations on the outer periphery (peanut shape).

What is claimed is:

1. A machine for winding sutures into a suture tray package, comprising:
   a base platform;
   a plurality of package nests;
   a first workstation for placing an empty tray onto one of the package nests;
   a further workstation for feeding a needle with an attached suture in the tray and parking said needle in the tray, the further workstation comprising at least two infeed lines for receiving infeed slides with needles and attached sutures;
   a winding station for winding the suture into a winding channel of the tray;
   a lid placement station for placing a lid onto one of the package nests;
   a lid attachment station for attaching the lid to the tray; and
   an offloading station for removing said trays from the package nests.

2. The winding machine according to claim 1, wherein the at least two infeed lines are exactly two infeed lines positioned at a 90 degree angle to each other.

3. The winding machine according to claim 1,
wherein said at least two infeed lines end at the same position.

4. The winding machine according to claim 1,
wherein one of said at least two infeed lines comes from an automated crimping unit.

5. The winding machine according to claim 1,
wherein one of said at least two infeed lines comes from a manual loading station.

6. The winding machine according to claim 1,
wherein the further workstation for feeding a needle in the tray and parking said needle in the tray comprises two tweezer grippers, and
wherein at least one of said tweezer grippers has a V- or U-shaped notch, said V- or U-shaped notch being located at an inside of the notched tweezer gripper facing the second tweezer gripper.

7. The winding machine according to claim 6,
wherein said V- or U-shaped notch is located at such a height of the notched tweezer gripper that the needle gripped with the tweezer grippers is held with a defined distance to the base of the tray.

8. The winding machine according to claim 6,
wherein said tweezer grippers rotate the gripped needle into the side of a foam park, said foam park being located at the base of the tray.

9. The winding machine according to claim 6,
wherein said tweezer grippers are gripping the needle from an infeed clamp, said infeed clamp being located on each infeed slide of the infeed slides.

10. The winding machine according to claim 9,
wherein there is a recessed area in the infeed slide, said recessed area being located in front of the infeed clamp in order to allow the tweezer grippers to dip into this recessed area when gripping the needle from the infeed clamp.

11. The winding machine according to claim 10,
wherein the recessed area of the infeed slide is designed as a cavity in the infeed slide.

* * * * *

UNITED STATES PATENT AND TRADEMARK OFFICE
CERTIFICATE OF CORRECTION

| | |
|---|---|
| PATENT NO. | : 11,278,275 B2 |
| APPLICATION NO. | : 16/564000 |
| DATED | : March 22, 2022 |
| INVENTOR(S) | : Dey et al. |

It is certified that error appears in the above-identified patent and that said Letters Patent is hereby corrected as shown below:

On the Title Page

Item (73) Assignee, Line 1, "Harra Höfliger" should read -- Harro Höfliger --

Item (73) Assignee, Line 3, "Allmorsbach im Tal (DE)" should read -- Allmersbach im Tal (DE) --

Signed and Sealed this
Twenty-fourth Day of May, 2022

Katherine Kelly Vidal
*Director of the United States Patent and Trademark Office*